United States Patent [19]
Liu

[11] Patent Number: 5,944,526
[45] Date of Patent: Aug. 31, 1999

[54] METHOD AND APPARATUS FOR A DENTAL IMPLANT SYSTEM

[76] Inventor: Chiaho Liu, 200 Thrush Ave., Crestline, Ohio 44827

[21] Appl. No.: 08/597,613

[22] Filed: Feb. 6, 1996

[51] Int. Cl.$^6$ ...................................................... A61C 8/00
[52] U.S. Cl. .............................................................. 433/176
[58] Field of Search .................................. 433/172, 173, 433/174, 175, 176

[56] References Cited

U.S. PATENT DOCUMENTS

| | | | |
|---|---|---|---|
| 3,082,525 | 3/1963 | Christensen | 433/174 |
| 3,436,826 | 4/1969 | Edelman | 433/75 |
| 3,579,829 | 5/1971 | Sampson | 433/173 |
| 4,121,340 | 10/1978 | Patrick | 433/176 |
| 4,379,694 | 4/1983 | Riess | 433/201 |
| 4,488,875 | 12/1984 | Niznick | 433/173 |
| 4,531,916 | 7/1985 | Scantlebury et al. | 433/173 |
| 4,702,697 | 10/1987 | Linkow | 433/173 |
| 4,741,698 | 5/1988 | Andrews | 433/173 |
| 4,828,492 | 5/1989 | Agnone | 433/173 |
| 5,098,296 | 3/1992 | Cullen | 433/173 |
| 5,133,662 | 7/1992 | Metcalfe | 433/176 |
| 5,178,539 | 1/1993 | Peltier et al. | 433/173 |
| 5,254,005 | 10/1993 | Zuest | 433/173 |
| 5,376,004 | 12/1994 | Mena | 433/173 |
| 5,513,989 | 5/1996 | Crisio | 433/176 |
| 5,564,924 | 10/1996 | Kwan | 433/173 |
| 5,769,898 | 6/1998 | Jisander | 433/173 |

*Primary Examiner*—John J. Wilson
*Attorney, Agent, or Firm*—Cesari & McKenna, LLP

[57] ABSTRACT

The dental implant system includes a saddle-shaped support member that fits over the patient's jaw bone and has a shallow depression into which an anchor for a prosthesis is inserted. A cover plate, with an opening for access to the anchor, fits over the anchor and a portion of the support. The system is held in place by retaining wires that wrap around the patient's jaw bone and over the cover plate. The wires supply rigidity to the system. The anchor is threaded, such that a crown abutment can be screwed to the anchor through the opening in the cover plate and thereby positioned on the jaw. The dental prosthesis is then attached to the crown abutment in a conventional manner.

23 Claims, 4 Drawing Sheets

METHOD AND APPARATUS FOR A DENTAL IMPLANT SYSTEM

FIELD OF THE INVENTION

The invention relates generally to devices for mounting a dental prosthesis, and more particularly, to a dental implant system that requires a minimal amount of bone structure for installation.

BACKGROUND OF THE INVENTION

As a result of disease or injury, many people suffer from a loss of permanent teeth. In severe cases, the surrounding oral tissue may be damaged as well. The loss of permanent teeth frequently limits the person's ability to chew food and may also appear unsightly. To fill the gap left by the lost teeth and to improve the person's ability to chew food, a dental prosthesis may be installed through oral surgery.

Ideally, the dental prosthesis is attached to the surrounding teeth. However, in situations where this is not possible, a dental implant is. installed and the prosthesis is mounted to the implant. As depicted in FIG. 1, one type of prior known implant 10 consists of a mounting stud 12 attached to a substructure 14 that is implanted into the patient's upper or lower jaw, i.e., the mandibular or maxillary structures. In order for the prosthesis (not shown) to withstand the significant occlusal forces exerted during mastication, the substructure 14 to which it is attached must be rigidly fixed in the jaw. The substructure 14 typically consists of a relatively long screw-type support 16, which has threads 18 and is screwed deeply through the cortical bone section 20 and into the cancellous bone section 22 of the jaw. The mounting stud 12, which rigidly attaches to the substructure 14 protrudes above the gum line 24, permitting the attachment thereto of the dental prosthesis.

There are several risks and limitations inherent in the use of this type of dental implant. First, the installation of the substructure 14 results in significant trauma to the jaw bone and risk of infection, because of the amount of drilling needed to seat the long screw support 16. Second, installation of the long screw support 16 risks damage to the mandibular nerve 26 which runs through the cancellous bone section 22 of the jaw or perforating the cancellous bone section 22. To minimize the risk of injury to the mandibular nerve 26 or of perforating the cancellous bone section 22 and to ensure adequate rigidity of the eventual prosthesis, the procedure is performed only if sufficient bone structure exists. Unfortunately, many patients lack the requisite bone structure in the area of the proposed prosthesis and are thus precluded from having this type of dental implant installed. As a result, these patients may be forced to undergo even greater reconstructive surgery, or forego a dental prosthesis altogether.

In addition to the above-referenced risks, expensive equipment that is suited only for the installation of these devices must be acquired. In particular, a drill that corresponds to the non-standard dimensions of the particular screw-type support being installed must be used to drill the necessary hole in the patient's jaw. Furthermore, a unique hand-piece is often required to install the screw support, which may have a non-standard head. As a result, the costs associated with installing a screw-type of implant can be significant.

SUMMARY OF THE INVENTION

It is an object of the present invention to provide a system for mounting a dental prosthesis that does not require the patient to present substantial bone structure.

The current dental implant system includes a saddle-shaped support member that fits over the patient's jaw bone and has a shallow depression into which an anchor for a prosthesis is inserted. A cover plate, with an opening for access to the anchor, fits over the anchor and a portion of the support. The system is held in place by retaining wires that wrap around the patient's jaw bone and over the cover plate. The wires provide the necessary rigidity to the implant system, thereby eliminating the need for a long screw-type substructure. The anchor is also threaded, such that a crown abutment can be screwed to the anchor through the opening in the cover plate and thereby positioned on the jaw. The dental prosthesis is then attached to the crown abutment in a conventional manner.

To implant the system, a dentist drills, on the ridge of the patient's jaw bone, a relatively shallow hole which is the size of the depression in the saddle-shaped support. The support is then placed over the jaw bone so that the depression rests in the hole. Next, the anchor is inserted into the depression, and the cover plate is positioned over both the anchor and a portion of the saddle-shaped support. Retaining wires are then guided around the patient's jaw bone and over the cover plate. The wires are drawn tightly around the jaw bone and fastened by twisting the two ends of each wire together at the cover plate. The implant system is thus rigidly secured to the patient's jaw.

Before installation of the crown abutment, a healing abutment may be attached to the anchor by a screw. The healing abutment provides a smooth surface to that portion of the jaw where the surgery was performed. Once the jaw has healed, the healing abutment is replaced with the crown abutment, which is similarly screwed to the anchor. A dental prosthesis is then attached directly to the crown abutment.

The current dental implant system can be installed with a minimal amount of bone structure because, unlike the prior known systems, it does not require a long screw-type substructure to provide the needed rigidity. Further, installation of the current system results in less trauma to the jaw bone since only shallow drilling is required to seat the depression of the saddle-shaped support into the patient's jaw. The shallow drilling also reduces the risk of damage to the patient's mandibular nerve. This is in contrast to the deep drilling required for insertion of the screw-type support of the prior systems, which may result in increased trauma to the jaw, damage to the mandibular nerve and/or perforation of the cancellous bone section.

The current dental implant system can also be installed with standard dental tools, avoiding any need to purchase unique installation tools. The shallow hole for receiving the depression of the saddle-shaped support member, for example, can be made using a standard drill available in most dental offices. The anchor and the cover plate, moreover, can be installed with standard dental tools, such as conventional dental pliers. Consequently, the cost of installing this implant system is substantially less, making the procedure available to more people.

BRIEF DESCRIPTION OF THE DRAWINGS

The above and further advantages of the invention may be better understood by referring to the following description in conjunction with the accompanying drawings, in which.

DETAILED DESCRIPTION OF THE PREFERRED EMBODIMENTS

Figure 2:
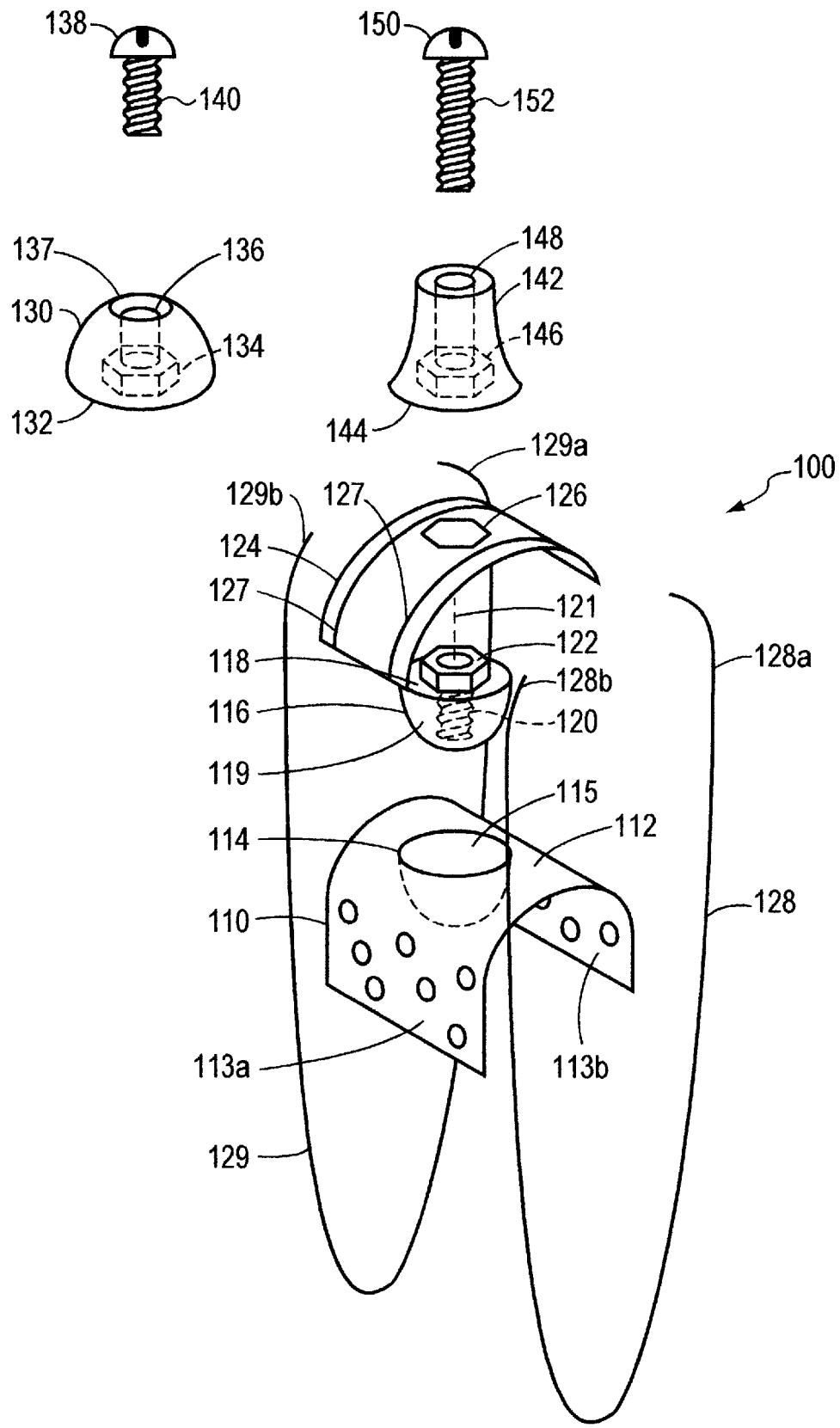
FIG. 2 is an isometric view of a preferred embodiment of the dental implant system of the present invention.
Figure 3:
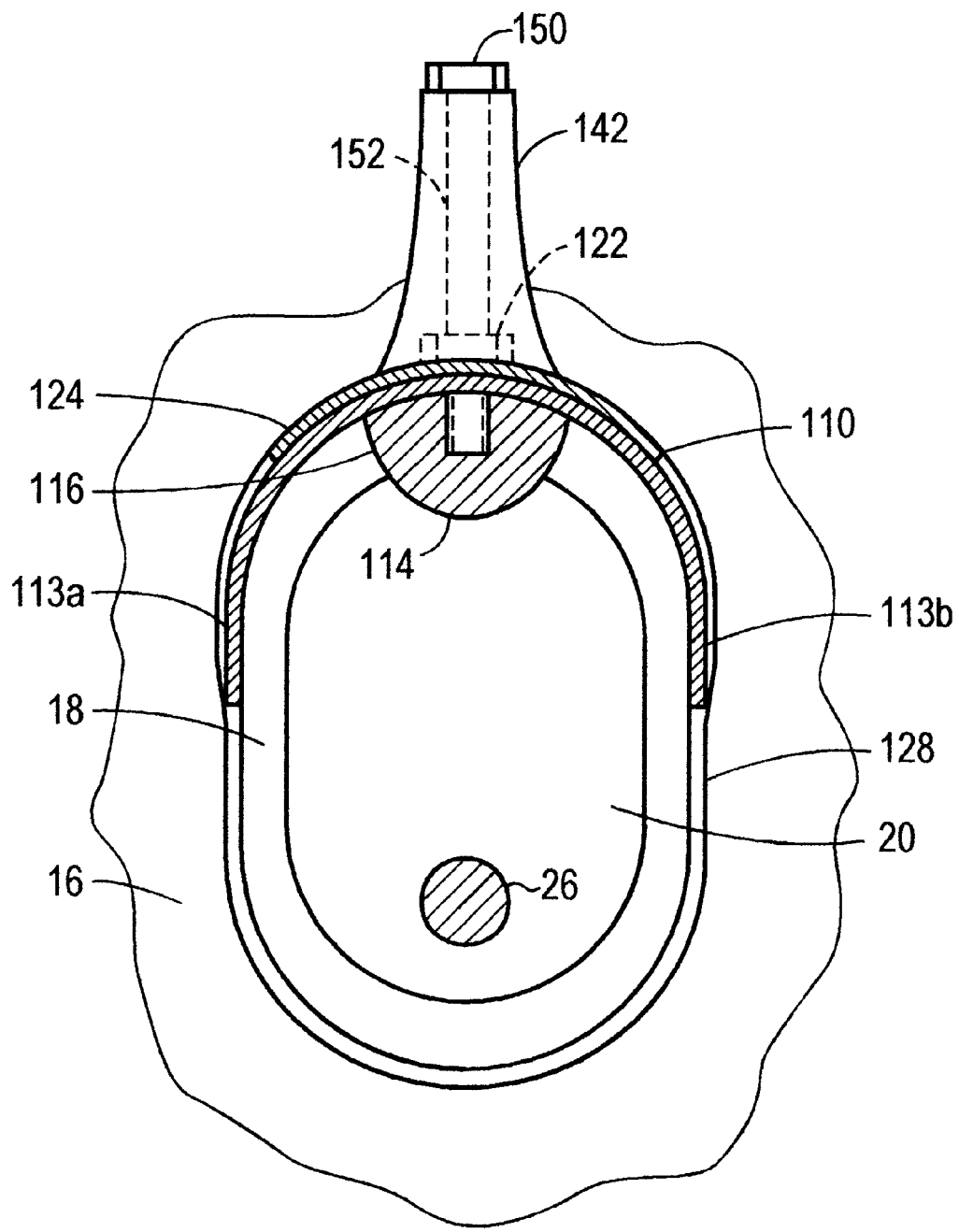
FIG. 3 is a cross section of a jaw bone showing the dental implant system of FIG. 2 as installed.

As shown in FIGS. 2 and 3, the dental implant system 100 of applicant's invention comprises a saddle-shaped support member 110, having a top center portion 112 and two side walls 113a and 113b. A relatively shallow depression 114, having a generally spherically-shaped inner surface 115, is formed in the top center portion 112 of the saddle-shaped support member 110 between the two side walls 113a, 113b. As discussed in more detail below, the saddle support 110 is positioned on the patient's jaw bone with the depression 114 resting in a shallow hole drilled by a surgeon or dentist.

An anchor 116, having a flat upper surface 118 and a spherically-shaped lower surface 119, fits into the depression 114, to permit a dental prosthesis (not shown) to be attached to the system 100. The anchor 116 includes a threaded hole 120 that extends perpendicularly into the anchor 116 from the upper surface 118. Mounted to the upper surface 118 of the anchor 116, in registration with the hole 120, is an alignment nut 122.

As the mating surfaces 115, 119 between the saddle support 110 and the anchor 116 are both spherically-shaped, the anchor 116 may be oriented within the depression 114 such that an axis (dotted line 121) extending through the hole 120 can be aligned with the surrounding teeth (not shown). This, in turn, ensures that the dental prosthesis will be aligned with the surrounding teeth.

A thin cover plate 124, having a matching opening 126 for the alignment nut 122, fits over both the anchor 116 and a portion of the saddle-shaped support 110. As shown in FIG. 3, when the cover plate 124 is placed over the anchor 116 and the support 110, the alignment nut 122 protrudes through the opening 126 and above the cover plate 124.

The cover plate 124 and the saddle-shaped support 110 are secured to the patient's jaw by means of at least two retaining wires 128 and 129. Each wire 128, 129 wraps around the patient's jaw and over the cover plate 124. The cover plate 124 may include two grooves 127 extending lengthwise along the top of the cover plate 124. The grooves 127 are formed on either side of the opening 126 for receiving the two retaining wires 128 and 129 that are wrapped over the cover plate 124. The grooves 127 also prevent the wires 128 and 129 from sliding off of the cover plate 124. As described in more detail below, the wires 128, 129 are secured by twisting corresponding ends 128a, 128b and 129a, 129b of each wire together preferably at the cover plate 124. The wires 128, 129 are drawn sufficiently tight around the jaw to hold the saddle-shaped support member 110, the cover plate 124 and thus, the anchor 116 rigidly in place.

It should be understood that rather than having two grooves, the cover plate may have two pairs of parallel, narrowly-spaced ridges extending lengthwise along the top of the cover plate on either side of the opening. Each pair of ridges is spaced to receive one of the retaining wires wrapped over the cover plate.

The saddle-shaped support member 110 is preferably perforated so that upon installation osseointegration may take place between the support member 110 and the jaw bone, to provide further rigidity to the dental implant system 100. Preferably, the support member 110 and the anchor 116 are made from titanium. The cover plate 124 is preferably formed of titanium or vitallium. The retaining wires 128 and 129 are preferably formed from stainless steel, titanium or vitallium.

Following installation of the dental implant system 100, a healing abutment 130 may be mounted to the system 100 above the cover plate 124 to improve the recovery process. The healing abutment 130 has a flat lower surface 132 in which a nut-shaped recess 134 is formed. A central hole 136 extends from top to bottom through the healing abutment 130. The healing abutment 130 is positioned over the cover plate 124 such that the alignment nut 122 is received within the recess 134. This aligns the central hole 136 of the healing abutment 130 with the threaded hole 120 of the anchor 116, and also prevents the healing abutment 130 from rotating or otherwise moving relative to the dental implant system 100.

A slotted, round-head screw 138 having a threaded portion 140 may be inserted into the through hole 136 of the healing abutment 130 and into the threaded hole 120 of the anchor 116. The threaded portion 140 of the screw 138 engages the threaded hole 120, thereby securely fastening the healing abutment 130 to the dental implant system 100. An upper recess 137 may be formed in the top of the healing abutment so that the head of the screw 138 is countersunk within the upper recess 137.

It should be understood that the screw 138 may be replaced with a bolt that is installed using a wrench rather than a screwdriver.

Following the healing process, the healing abutment 130 may be replaced with a crown abutment 142. The crown abutment 142 has a lower surface 144 in which a nut-shaped recess 146 is formed. A central hole 148 extends from top to bottom through the crown abutment 142. When the crown abutment 142 is positioned onto the dental implant system 100 above the cover plate 124, the alignment nut 122 is received within the recess 146 of the crown abutment 142. This aligns the hole 148 in the crown abutment 142 with the threaded hole 120 of the anchor 116, and prevents the crown abutment 142 from rotating or otherwise moving relative to the dental implant system 100.

A slotted, round-head retaining screw 150 having a threaded portion 152 may be inserted into the through hole 148 of the crown abutment 142 and into the threaded hole 120 of the anchor 116. The threaded portion 152 of the retaining screw 150 engages the threaded hole 120, thereby securely fastening the crown abutment 142 to the dental implant system 100. The retaining screw 150 is preferably formed from gold.

It should be understood that a second recess may be formed in the top of the crown abutment 142 so that the head of the retaining screw 150 is countersunk within the second recess. It should be further understood that the alignment nut 122 may be threaded so that the alignment nut 122, as well as the threaded hole 120, engages the retaining screw 150.

A dental prosthesis (not shown) may be attached to the crown abutment 142.

Figure 4A:
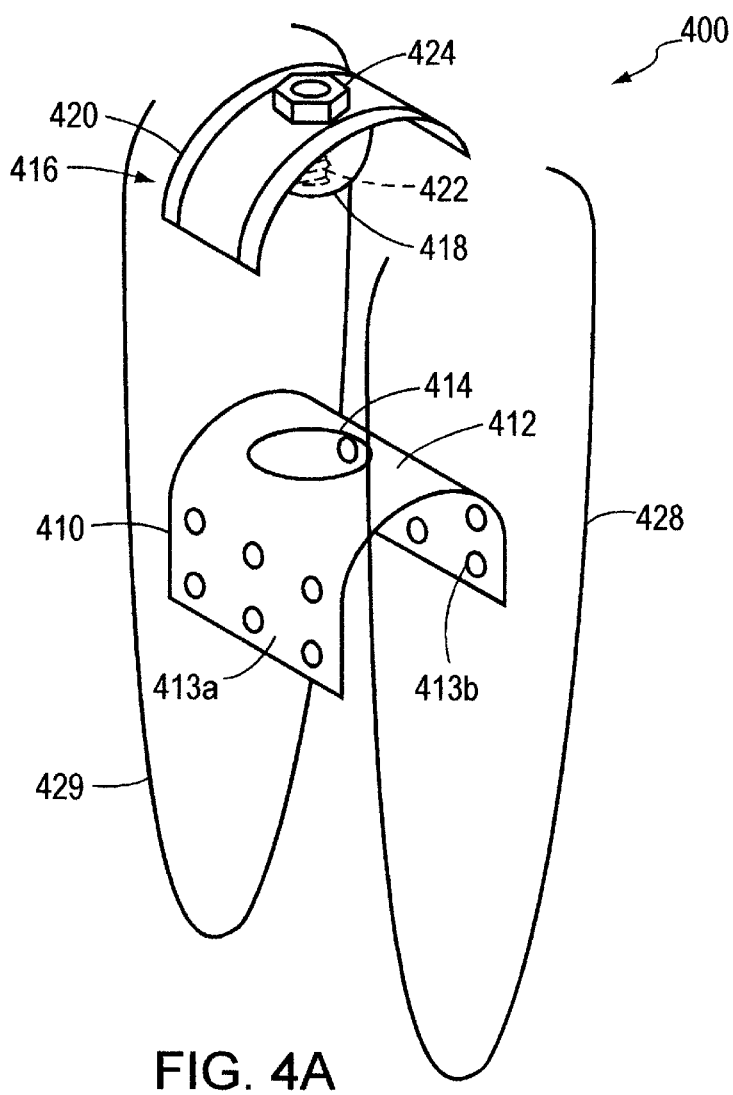
FIG. 4A is an isometric view of a second embodiment of the dental implant system of the present invention.
Figure 4B:
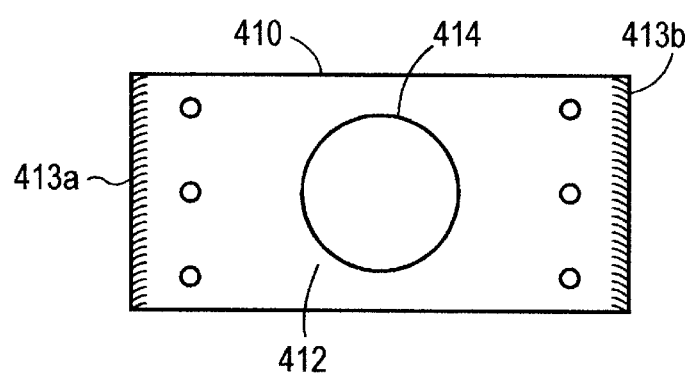
FIG. 4B is a side view of a portion of the system of FIG. 4A.

FIGS. 4A and 4B show a second embodiment of the dental implant system 400 of the present invention. The dental implant system 400 includes a saddle-shaped support member 410 having a top center portion 412 and two side walls 413a and 413b. In this embodiment, the saddle-shaped support member 410 includes a circular receiving hole 414, rather than a spherically-shaped depression 114 of FIG. 2.

A combined anchor/plate member 416 includes a thin cover plate 420 and a substructure 418 that fits into the receiving hole 414. A threaded hole 422 extends downwardly through the cover plate 420 and into the substructure 418. Mounted to the cover plate 420 opposite the substructure 418 is an alignment nut 424. The alignment nut 424 is mounted in registration with the threaded hole 422.

The combined anchor/plate member 416 is positioned onto the saddle-shaped support 410 so that the substructure 418 fits within the receiving hole 414 and the cover plate 420 extends over a portion of the saddle support 410. The combined anchor/plate member 416 is secured to the saddle support 410 by at least two retaining wires 428 and 429. The retaining wires 428 and 429 wrap over the cover plate 420 and around the patient's jaw bone.

Rather than having the cover plate integral with the anchor, it should be understood that the anchor may include a generally circular flange extending around the upper surface, such that the flange, as opposed to the integral cover plate, supports the anchor within the receiving hole.

Figure 1:
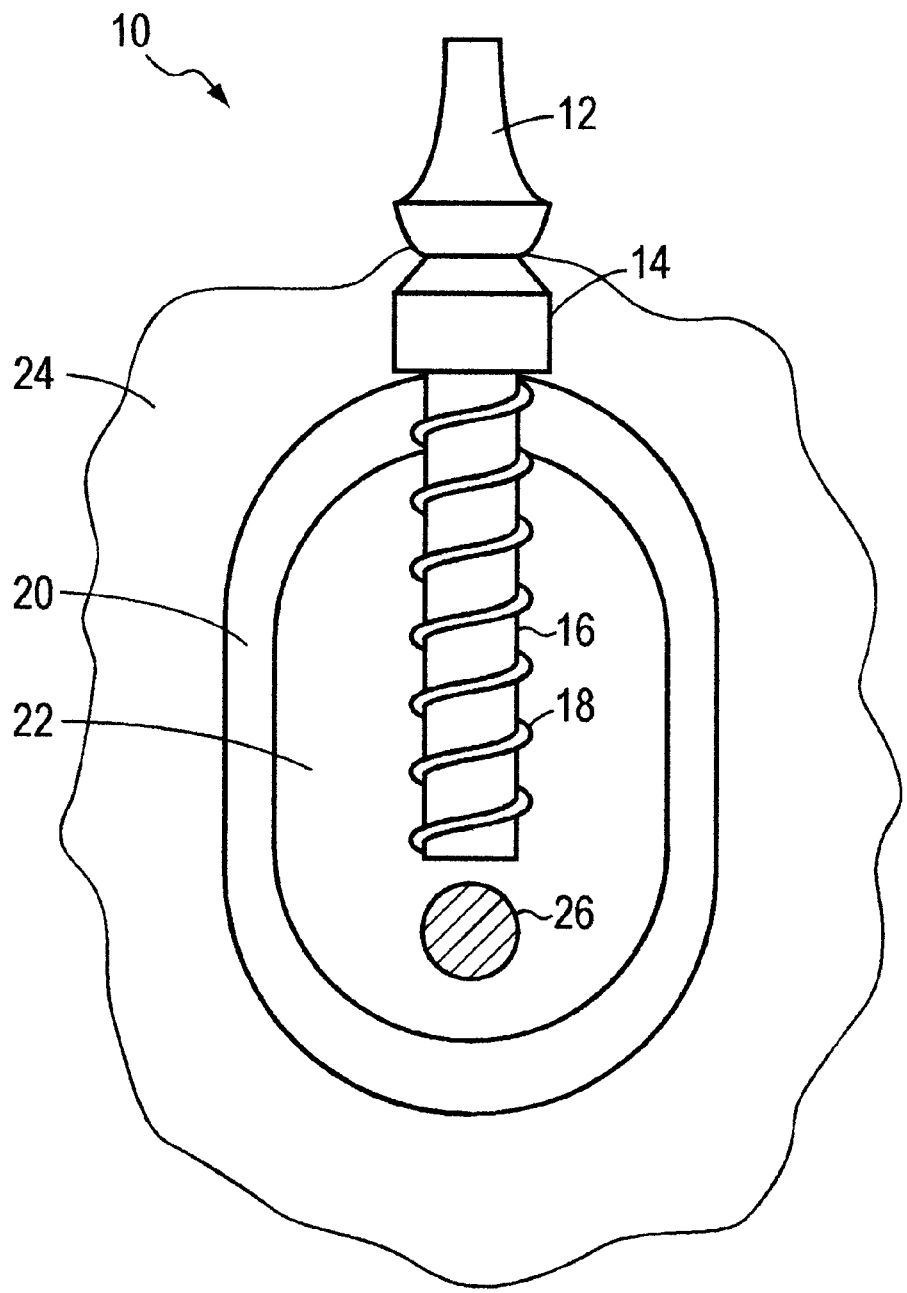
FIG. 1, discussed above, is a cross section of a jaw bone showing a prior art dental implant device.

The current dental implant system 100 is designed to be installed at any location in the jaw where a dental prosthesis is needed, including locations where bone erosion or bone loss due to disease or injury has occurred. In contrast, the prior screw-type implant device, discussed above with reference to FIG. 1, requires that substantial bone structure exist at the implant site. The current dental implant system 100 can also be installed at an extraction site by simply placing the saddle support 110 over the extraction site. The prior screw-type support may be installed at an extraction site, but still requires drilling to rigidly seat the support.

Although the precise dimensions of the current system 100 can be modified to conform to the dimensions of the particular patient's jaw structure, the average depth of the depression 114 is approximately 3.0 mm as opposed to the prior art screw-type support which is on the order of 6–12 mm long. Nonetheless, by virtue of the retaining wires 128, 129, the dental implant system 100 provides a sufficiently rigid mounting point for the dental prosthesis. Moreover, as shown in FIG. 3, the dimensions of the depression 114, and in particular its shallow depth, ensure that the dental implant system 100 poses a much lower risk of either damaging the patient's mandibular nerve 26 or perforating the surrounding bone of the mandible than the prior system of FIG. 1.

The method of installing the dental implant system 100 is as follows. First, the tissue overlying that portion of the jaw bone where the dental implant system 100 is to be installed must be pulled back to expose the alveolar ridge of the jaw bone. To obtain this result, a dentist or oral surgeon makes a beveled incision slightly lingual to the crest of the soft-tissue ridge of the jaw, thereby freeing two flaps of tissue that extend deeply into the buccal mucosa. Using blunt dissection, the surgeon pulls back the two flaps of tissue exposing the alveolar ridge of the jaw bone. The two flaps of tissue are then tied back with sutures to maintain visibility of the surgical field.

Next, at a pre-selected point on the alveolar ridge, the surgeon drills a hole approximately 3 mm deep through the cortical bone section 18 and into the cancellous bone section 20 of the jaw, for receiving the depression 114 of the saddle-shaped support member 110. To avoid damaging the bone, the surgeon uses circular or oval cutting drills and burs run at slow speed and cooled with saline. Ideally, the installation point on the alveolar ridge is relatively flat so that the saddle-shaped support member 110 will fit on the ridge without rocking. If necessary, the area can be modified, prior to drilling, by performing an alveoplasty ridge procedure, for example.

Once the hole has been prepared, the saddle-shaped support member 110 is installed, so that the depression 114 rests in the hole and the side walls 113a, 113b extend along the buccal and lingual aspects of the jaw bone. With the saddle-shaped support member 110 in place, the surgeon verifies that the upper surface of the saddle-shaped support member 110 is flush with the alveolar ridge. Any irregularities in the alveolar ridge may be corrected with fillers, e.g., HA (hydroxyapetipe) fillers or freeze dried bone or other natural or synthetic bone fillers.

Next, the surgeon installs the anchor 116 and the cover plate 124. First, he inserts the anchor 116 into the depression 114 in the saddle-shaped support member 110 with the alignment nut 122 facing out. He then orients the anchor 116 within the depression 114 so that the axis 121 of the hole 120 extending through the anchor 116 (and thus, the eventual dental prosthesis) is in line with the surrounding teeth. Next, he places the cover plate 124 over the anchor 116, so that the alignment nut 122 protrudes through the matching opening 126 in the cover plate 124, and bends the plate 124 to fit over the saddle support 110. The cover plate 124 is then burnished to conform to the top portion of the saddle-shaped support 110, and any excess portions of the cover plate 124 are cut and removed.

The saddle-shaped support 110, the anchor 116 and the cover plate 124 are then secured to the patient's jaw with the retaining wires 128 and 129. The surgeon inserts the first retaining wire 128 into a wire holder, which may be similar to, but smaller than the Howmedica No. 3812-2-290 wire holder, so that both ends 128a and 128b of the wire 128 are retained by the wire holder. The surgeon then makes an incision at a point on the inferior border of the mandible below the saddle support 110, i.e., on the patient's outer skin underneath the implant site, for insertion of the wire holder. The surgeon then inserts the wire holder through the incision and slides it along the buccal aspect of the jaw bone until the tip of the wire holder is seen in the buccal aspect of the surgical field. The first end 128a of the wire 128 is then threaded through the wire holder and grasped by the surgeon.

While holding one end 128a of the wire 128, the surgeon draws the wire holder away from the surgical field but not out of the incision and slowly slides it first underneath and then up along the lingual aspect of the jaw bone until the tip of the wire holder is seen in the lingual aspect of the surgical field. The other end 128b of the wire 128 is then threaded through the wire holder and grasped by the surgeon so that the wire 128 now wraps around the patient's jaw. Using both ends 128a, 128b of the wire 128, the surgeon pulls the wire 128 taut and, making sure that the wire 128 wraps over the cover plate 124 and is within the groove 127, fastens the wire 128 by twisting the two ends 128a, 128b together, preferably at the cover plate 124. It should be understood that the wire 128 should be as perpendicular to the length of the jaw bone as possible. Any excess portions of the retaining wire 128 are thereafter removed and the twisted portion of the wire 128 is bent flush with the cover plate 124. This process is repeated for the second retaining wire 129, which is positioned in the groove 127 on the opposite side of the opening 126 from the first wire 128. The two retaining wires 128, 129 give the system 100 rigidity, and thus, eliminate the need to insert the anchor 116 deeply into the jaw bone.

With the dental implant system 100 secured to the jaw bone by the retaining wires 128 and 129, the next step is to install the healing abutment 130. The surgeon places the healing abutment 130 onto the cover plate 124 of the dental implant system 100 so that the alignment nut 122 is received within the recess 134 of the healing abutment 130. The surgeon then inserts the screw 138 through the healing abutment 130 and into the threaded hole 120 of the anchor 116. A screwdriver may be used to tighten the screw 138, thereby securely fastening the healing abutment 130 to the dental implant system 100. The two flaps of tissue are then repositioned and sutured so that they cover the healing abutment 130. If the flaps are too small to cover the healing abutment 130, the surgeon can perform a z-plasty procedure.

Once the soft tissue surrounding the incision has healed, the surgeon removes the healing abutment 130. The healing process generally takes one to two weeks. It should be understood that the time to complete the healing process may vary from patient to patient and that the final determination of sufficient recovery rests with the surgeon. Although it is preferred to wait until osseointegration occurs between the jaw and the implant system 100 (which may take from six to eight months) before installing the crown abutment 124 and the dental prosthesis, the patient may elect to proceed with installation of the crown abutment and the dental prosthesis as soon as the soft tissue has healed. The surgeon removes the healing abutment 130 using a screwdriver to back the screw 138 out of engagement with the anchor 116. A small incision in the tissue may have to be made to access the healing abutment 130.

With the healing abutment 130 removed, the surgeon installs the crown abutment 142 to the dental implant system 100. First, the crown abutment 142 is temporarily placed onto the cover plate 124 to determine whether enough clearance exists between the top of the crown abutment 142 and the proposed dental prosthesis. If not, the crown abutment 142 may be shortened using a rotary instrument. The retaining screw 150 can be correspondingly shortened by removing a bottom fraction of the threaded portion 152.

The surgeon then places the crown abutment 142, which has been modified as necessary, over the cover plate 124, so that the alignment nut 122 is received within the recess 146 of the crown abutment 142. The surgeon inserts the retaining screw 150 through the central hole 148 of the crown abutment 142 and into engagement with the threaded hole 120 of the anchor 116. A screwdriver may be used to tighten the retaining screw 150, thereby securely fastening the crown abutment 142 to the dental implant system 100. The surgeon then repositions and sutures the tissue. A dental prosthesis is then attached to the crown abutment in a conventional manner.

The foregoing description has been directed to specific embodiments of this invention. It will be apparent, however, that other variations and modifications may be made to the described embodiment, with the attainment of some or all of their advantages. Therefore, it is the object of the appended claims to cover all such variations and modifications as come within the true spirit and scope of the invention.

What is claimed is:

1. A dental implant system for use in mounting a dental prosthesis to a patient's jaw, the system comprising:
    an anchor, having an upper surface and a threaded hole extending into the anchor from the upper surface;
    a saddle-shaped support member having two side walls separated by a top center portion, the top center portion including a shallow depression that extends downwardly between the two side walls and is configured to receive the anchor therein;
    a cover plate overlaying both the anchor and at least a portion of the top center portion so as to retain the anchor within the shallow depression; and
    means for securing the cover plate and the saddle-shaped support member to the patient's jaw.

2. The dental implant system of claim 1 further comprising:
    an alignment nut mounted to the upper surface of the anchor in registration with the threaded hole, and
    an opening disposed in the cover plate,
    wherein the opening matches the alignment nut.

3. The dental implant system of claim 2 further comprising:
    a healing abutment having a central hole, a lower surface and a recess formed in the lower surface, the recess for receiving the alignment nut,
    wherein the healing abutment is removably attached to the anchor above the cover plate.

4. The dental implant system of claim 3 further comprising a screw, wherein the healing abutment is removably attached to the anchor above the cover plate by inserting the screw through the central hole and engaging the threads of the threaded hole in the anchor.

5. The dental implant system of claim 2 further comprising:
    a crown abutment having a central hole, a lower surface and a recess formed in the lower surface, the recess for receiving the alignment nut, and
    a retaining screw,
    wherein the crown abutment is attached to the anchor above the cover plate by inserting the retaining screw through the central hole and engaging the threads of the threaded hole in the anchor.

6. The dental implant of claim 5 wherein the retaining screw has a lower end such that, with the crown abutment attached to the anchor, the screw's lower end does not extend through the support member.

7. The dental implant system of claim 1 wherein the securing means comprises at least two retaining wires, each wire having two ends, wherein each retaining wire is wrapped over the cover plate for wrapping around the patient's jaw bone and the ends of each wire are twisted together.

8. The dental implant system of claim 7 wherein the cover plate has two grooves extending lengthwise across the top of the cover plate wherein each groove receives a retaining wire which is wrapped over the cover plate.

9. The dental implant system of claim 1 further comprising a healing abutment removably attached to the anchor.

10. The dental implant system of claim 1 further comprising a crown abutment attached to the anchor.

11. The dental implant system of claim 1 wherein the depression has a depth of approximately 3 millimeters.

12. The dental implant system of claim 1 wherein:
    the receiving means comprises a hole in the saddle-shaped support member, and
    the anchor further includes a cover plate that extends outwardly from the upper surface of the anchor, the cover plate having an opening for access to the threaded hole,
    wherein the cover plate supports the anchor in the hole in the saddle-shaped support and overlays a portion of the saddle support.

13. The dental implant of claim 1 wherein the threaded hole of the anchor defines a longitudinal axis and the anchor and depression further include mating surfaces that cooperate to allow the axis of the threaded hole to be freely oriented relative to the support member.

14. The dental implant of claim 13 wherein the mating surfaces are semi-spherical.

15. The dental implant of claim 1 wherein the anchor is free of interlocking engagement with the patient's jaw.

16. A. A dental implant system for use in mounting a dental prosthesis to a patient's jaw, the system comprising:

a saddle-shaped support member, having a top center portion, two side walls and a depression formed in the top center portion between the two side walls;

an anchor, having a generally flat upper surface and a threaded hole extending into the anchor perpendicular from the upper surface, the anchor being inserted into the depression;

an alignment nut mounted to the upper surface of the anchor in registration with the threaded hole;

a cover plate, having a matching opening for the alignment nut, the cover plate overlaying the anchor and a portion of the saddle-shaped support such that the alignment nut protrudes through the opening; and at least two retaining wires, for-wrapping tightly around the patient's jaw and over the cover plate to secure the saddle-shaped support member, the anchor and the cover plate to the patient's jaw.

17. A method of installing a dental implant system in a patient's jaw for use in mounting a dental prosthesis, comprising the steps of:

drilling out a bore in the jaw at a pre-selected point on the patient's jaw, the bore being shaped to receive an anchor;

placing a saddle-shaped support member, having a means for receiving the anchor, over the patient's jaw, such that the receiving means rests in the bone;

inserting the anchor, having an alignment nut mounted to an upper surface, in the receiving means of the saddle-shaped support so that the alignment nut faces out;

placing a cover plate, having an opening for receiving the alignment nut, over the anchor and a portion of the saddle-shaped support member, so that the alignment nut protrudes through the opening; and securing the cover plate, anchor and saddle-shaped support member to the jaw with at least two retaining wires.

18. The method of claim 17 further comprising the step of removably attaching a healing abutment to the anchor above the cover plate.

19. The method of claim 18 further comprising the step of replacing the healing abutment with a crown abutment attached to the anchor above the cover plate.

20. The method of claim 17 wherein the step of securing comprises:

locating an insertion point on the patient's inferior border of a mandible below the saddle support;

inserting a first retaining wire into a wire holder;

inserting the wire holder with the wire through an incision in the patient's skin at the previously located insertion point;

sliding the wire holder along a buccal aspect of the jaw bone until a tip of the wire holder is seen in the buccal aspect of a surgical field;

threading a first end of the wire through the wire holder;

grasping the end of the wire;

drawing the wire holder away from the surgical field but not out of the insertion point;

sliding the wire holder first underneath and then up along a lingual aspect of the jaw bone until the tip of the wire holder is seen in a lingual aspect of the surgical field;

threading a second end of the wire through the wire holder;

grasping the first and second ends of the wire;

pulling the first and second ends to tighten the wire about the jaw bone, to secure the cover plate and saddle-shaped support to the jaw bone; and fastening together the first and second ends of the wire.

21. A dental implant system for use in mounting a dental prosthesis to a patient's jaw, the system comprising:

a saddle-shaped support member;

an anchor, having an upper surface and a threaded hole extending into the anchor from the upper surface;

means for receiving the anchor in the saddle-shaped support member; means for securing the anchor and the saddle-shaped support member to the patient's jaw; and a cover plate wherein the cover plate overlays the anchor and a portion of the saddle-shaped support member, wherein the securing means comprises at least two retaining wires, each wire having two ends, wherein each retaining wire is wrapped over the cover plate for wrapping around the patient's jaw bone and the ends of each wire are twisted together.

22. The dental implant system of claim 21 wherein the cover plate has two grooves extending lengthwise across the top of the cover plate wherein each groove receives a retaining wire which is wrapped over the cover plate.

23. A dental implant system for use in mounting a dental prosthesis to a patient's jaw, the system comprising:

an anchor, having an upper surface, a threaded hole extending into the anchor from the upper surface and a cover plate that extends outwardly from the upper surface of the anchor, the cover plate having an opening providing access to the threaded hole;

a saddle-shaped support member having a hole to receive the anchor therein; and means for securing the anchor and the saddle-shaped support member to the patient's jaw, wherein the cover plate supports the anchor in the hole in the saddle-shaped support and overlays a portion of the saddle support.

* * * * *